United States Patent
Jansen et al.

(10) Patent No.: US 7,632,278 B2
(45) Date of Patent: Dec. 15, 2009

(54) SERRATOME VERTEBRAL CORTICAL ENDPLATE CUTTER

(75) Inventors: Keith E. Jansen, Pembroke, MA (US); Andrew R. Sennett, Hanover, MA (US)

(73) Assignee: Alphatec Spine, Inc., Carlsbad, CA (US)

( * ) Notice: Subject to any disclaimer, the term of this patent is extended or adjusted under 35 U.S.C. 154(b) by 447 days.

(21) Appl. No.: 11/012,770

(22) Filed: Dec. 15, 2004

(65) Prior Publication Data
US 2005/0131416 A1 Jun. 16, 2005

Related U.S. Application Data

(62) Division of application No. 10/292,159, filed on Nov. 12, 2002, now abandoned.

(51) Int. Cl.
*A61F 5/00* (2006.01)
*A61F 2/44* (2006.01)
(52) U.S. Cl. .................. 606/86 A; 632/17.11
(58) Field of Classification Search .......... 606/84, 606/87, 79, 61, 86, 86 A; 30/168, 167, 170, 30/167.1; 144/88, 70, 75, 78; 408/30; 623/17.11
See application file for complete search history.

(56) References Cited

U.S. PATENT DOCUMENTS

| 824,673 | A | * | 6/1906 | Rockwell | 30/167.1 |
| 2,487,221 | A | * | 11/1949 | Cooke | 606/84 |
| 4,743,256 | A | | 5/1988 | Brantigan | 128/898 |
| 5,405,349 | A | | 4/1995 | Burkinshaw et al. | 606/88 |
| 5,540,693 | A | | 7/1996 | Fisher | 606/79 |
| 5,571,109 | A | * | 11/1996 | Bertagnoli | 606/61 |
| 5,573,537 | A | * | 11/1996 | Rogozinski | 606/80 |
| 5,722,977 | A | * | 3/1998 | Wilhelmy | 606/84 |
| 5,725,531 | A | | 3/1998 | Shapiro | 606/85 |
| 6,241,733 | B1 | * | 6/2001 | Nicholson et al. | 606/84 |
| 6,485,495 | B1 | * | 11/2002 | Jenkinson | 606/84 |
| 6,641,582 | B1 | * | 11/2003 | Hanson et al. | |
| 7,147,642 | B2 | * | 12/2006 | Grinberg et al. | 606/79 |

* cited by examiner

*Primary Examiner*—Pedro Philogene
(74) *Attorney, Agent, or Firm*—Mintz, Levin, Cohn, Ferris, Glovsky and Popeo PC

(57) ABSTRACT

The invention relates to spinal fusion implants or grafts and to apparatus for the installation thereof. More specifically, the invention is a serrated cutting or abrading tool designed to be pushed into an intervertebral space and thereby remove and partially penetrate the cortical bone layer that defines the endplates of the respective mutually adjacent vertebral bodies.

7 Claims, 4 Drawing Sheets

SERRATOME VERTEBRAL CORTICAL ENDPLATE CUTTER

This application is a divisional of U.S. patent application Ser. No. 10/292,159, filed Nov. 12, 2002 now abandoned, and claims priority based on that application.

FIELD OF INVENTION

This invention relates generally to the treatment of injured, degenerated, or diseased tissue in the human spine. More specifically, the present invention relates to spinal fusion, and most specifically it relates to preparation of the intervertebral site to receive a spinal-fusion bone implant.

BACKGROUND OF THE INVENTION

For many years a treatment, often one of last resort, for serious back problems has been spinal fusion surgery. Disc surgery, for example, typically requires removal of a portion or all of an intervertebral disc, which must then be replaced by a stabilizing structural element, such as a bony graft implant, that can maintain the separation between the vertebrae being fused so as to obviate damage to the spinal cord and adjacent nerves.

The most common sites for such surgery, namely those locations where body weight exerts its greatest loads on the spine, are in the lumbar region and immediately below, namely the vertebrae L1-2, L2-3, L3-4, L4-5, and L5-S1. However, other sites, for example the cervical vertebrae, are susceptible to related problems which also may require surgery and implants. In addition, a number of degenerative diseases and other conditions such as scoliosis require correction of the relative orientation of vertebrae, wherever they are located, by surgery and fusion.

In general for spinal fusions a significant portion of the intervertebral disk is removed and a stabilizing element, frequently including bone graft material, is inserted into the intervertebral space. It has been found in recent years that metal cages do not reliably produce fusion because they shield inserted bone growth material from the compressive loading that has been found to be necessary to promote new bone growth. Accordingly, other types of implants, especially those fabricated from autograft and allograft bone, have come into use. An example is the allograft implant of Nicholson, et al., U.S. Pat. No. 6,096,080, issued Aug. 1, 2000, which is an interlocking dovetail shaped device. Other forms of allograft and autograft implants are simply rectangular, cylindrical, or disc shaped and require no particular preparation of the adjacent vertebral end plates. Such bone grafts shapes are sometimes contoured to ride on the end plates of the vertebral bodies.

It has been found, however, that preparation of the end plates materially improves the fusion rate. Typically the surgeon prepares the vertebrae to be fused by breaking through, or cutting into, the hardened end plate surfaces of vertebral bone so as to allow an interposed bone graft or implant to come into direct contact with the cancellous (spongy) portion of the vertebral bone. Practitioners believe that this procedure produces superior results, first because it enables more intimate surface mating of the implant with the existing bone. Second, and more important, however, the cancellous bone interior to the vertebrae is vascularized, so that in the right circumstances blood will flow through the implant. Practitioners also believe that the clotting of blood inside such an implant is the first step of new bone growth. It is thought, therefore, that controlled "fracturing" of the vertebral endplates allows new bone generation to take place and for the incorporation of inserted bone grafts or implants into the two respective adjacent vertebral surfaces such that they become one continuous and rigid segment of bone.

In some cases, such as the dovetail implant, specialized cutting devices shaped specifically for that device will be provided. However, for more general shapes, such as discs and rectangular implants, it is not always possible to provide specialized instrumentation.

It is an object of the current invention to provide a method and an apparatus which can provide rapid and efficient preparation of an intervertebral space to receive an implant of a wide variety of shapes and configurations. It is another object of the present invention is to provide a device that can remove a sufficient amount of hard cortical bone from the respective endplates of the vertebral bodies so that blood from within the bones' medullar region can flow into and commence clotting within the region where the implant is to be installed. A further object of the present invention is to prepare the implant site in a way that does not destroy the structural integrity of or remove the endplate, but rather only abrades away as sufficient amount of the cortical material so that blood from the medullar regions can move into the region of the implant. Yet another more specific object of the invention is to provide a serrated cutting device that can be inserted into an intervertebral space in such a way as to remove controlled amounts of cortical bone simultaneously from the respective endplates of the two vertebral bodies being fused. And yet another objective of the present invention is to provide a method by which to keep the serrated cutting device from penetrating too deep into the intervertebral space. And a final objective of the present invention is to provide a method and a device for driving the serrated cutter into the intervertebral space with the least trauma to the spine.

SUMMARY OF INVENTION

The present invention, which is called a SERRATOME™, is a bone-scraping or cutting device designed to be driven into an intervertebral space so as to remove, by cutting and/or abrading, a sufficient amount of end plate cortical bone of two adjacent vertebral bodies to allow blood to flow into the intervertebral space from the cancellous region of the respective vertebral bodies. Establishment of the flow of blood from within the adjacent vertebral bodies, and the initiation of the clotting of that blood, can be sufficient preparation of the intervertebral site for the installation of an allograft implant. That is, the flow of blood into the implant and the intervertebral space around it will initiate clotting in and around the implant, which clotting is believed to promote new bone growth.

The present invention prepares the implant site in a way that does not destroy or remove a large amount of endplate cortical material, but rather scrapes away only an amount of the cortical material sufficient for blood from the cancellous regions to seep into the region where the allograft implant is to be installed. Once the flow of blood has been established, the region is prepared to receive an implant of a wide variety of shapes and configurations.

More specifically, the invention is a serrated cutting or abrading tool designed to be pushed into an intervertebral space and thereby remove and partially penetrate the cortical bone layer that defines the endplates of the respective mutually adjacent vertebral bodies. In its simplest form, the invention comprises a hollow rectangular solid having sharp serrations or teeth on the top and bottom surfaces. When the invention is inserted into an intervertebral space, the upper and lower sets of serrations impact against and remove by scraping portions of the cortical bone of the respective endplates of the vertebral bodies.

In another embodiment, the invention employs the use of a blunted front region that is located forward of the serrated teeth and projects out ahead of the main body of the serrate cutter. The outward-projected blunt front region provides guidance of the serrate cutter into the intervertebral space while simultaneously distracting and seperating the vertebral bodies. The outward-projected blunt front region may have may shapes including that of a parabola.

Another embodiment of the invention employs a handle affixed to the distal end of the serrate cutter. The handle may have affixed to its end most distal from the serrate cutter an anvil suitable for use with a mallet driver, or it may have affixed to it a simple handle which the surgeon can grasp so as to push the serrate into the intervertebral space for a single manual cutting motion or additional cutting motions. Additionally, the handle might have affixed to its distal end a pneumatic or hydraulic or other vibrating driver device that can, in an easily controllable way, allow the surgeon to move the serrate in its intended linear motions in the most efficient, safe and controllable way.

In another embodiment, the invention employs a stop that is either part of the handle or an intervening element that is joined between the serrate cutter and the handle portion. The stop prohibits the serrate cutter from going too deep into the intervertebral space, so as to minimize the risk of damage to the spinal cord lying anterior to the main portions of the vertebral bodies.

IDENTIFICATION OF ITEMS IN THE FIGURES

Figure 1:
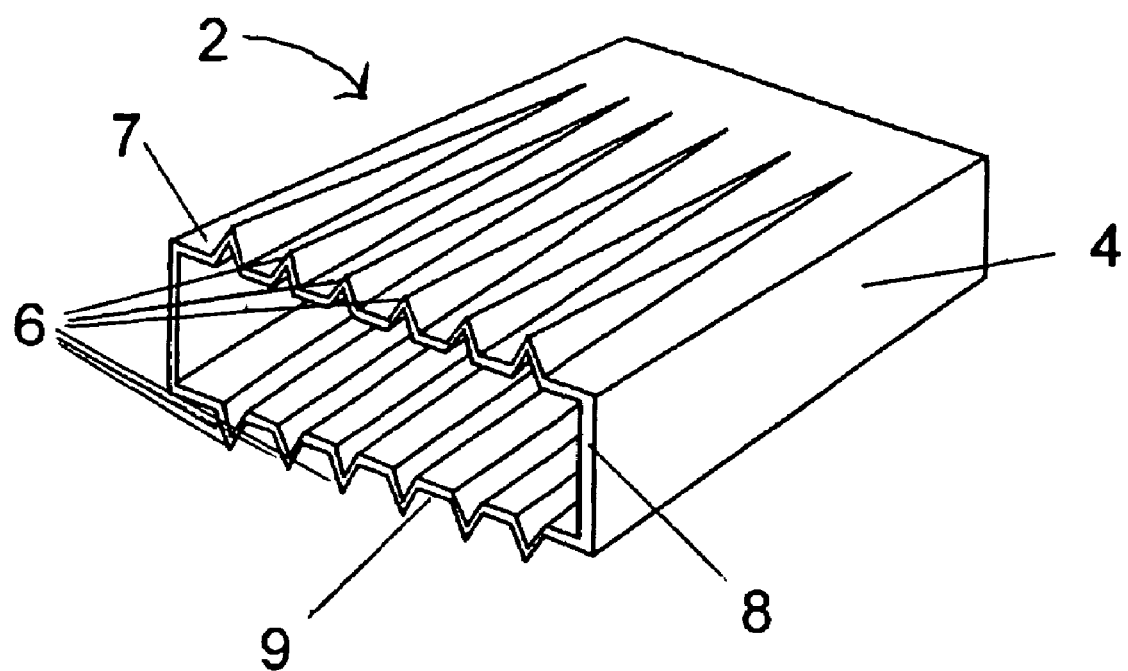
FIG. 1 is an oblique perspective view of the SERRATOME™ invention.
Figure 2A:
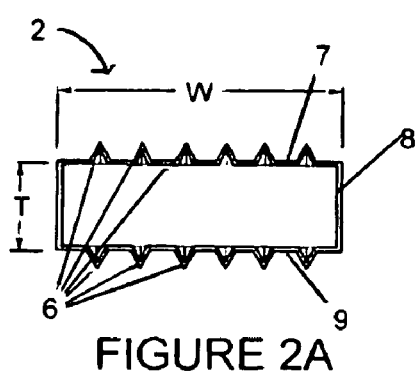
FIG. 2A is an orthogonal front view of the present SERRATOME™ invention.
Figure 2B:
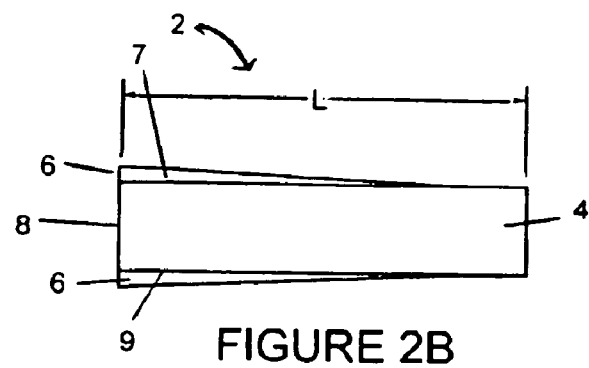
FIG. 2B is an orthogonal side view of the present SERRATOME™ invention.
Figure 2C:
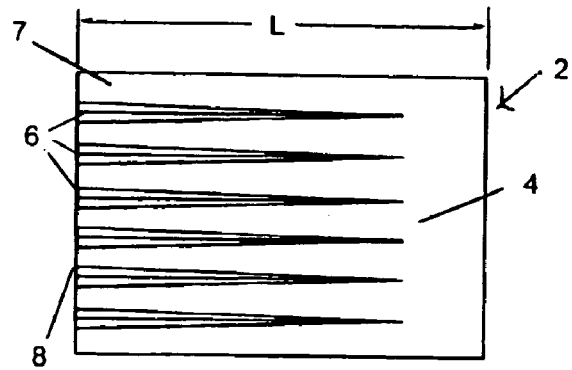
FIG. 2C is an orthogonal top view of the present SERRATOME™ invention.

FIG. 1
2—SERRATOME™
4—main body
6—serrations
7—top face of body
8—sharpened front cutting edge of SERRATOME™
9—bottom face of body FIG. 2A
2—SERRATOME™
6—serrations
7—top face of body
8—sharpened front cutting edge of SERRATOME™
9—bottom face of body FIG. 2B
2—SERRATOME™
4—main body
6—serrations
7—top face of body
8—sharpened front cutting edge of SERRATOME™
9—bottom face of body FIG. 2C
2—SERRATOME™
4—main body
6—serrations
7—top face of body
8—sharpened front cutting edge of SERRATOME™

Figure 3A:
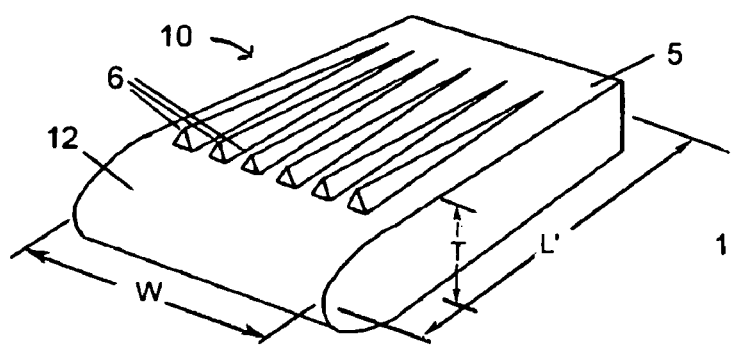
FIG. 3A is an oblique perspective view of the present SERRATOME™ invention with a blunt front end.

FIG. 3A
5—main body
6—serrations
10—SERRATOME™
12—blunt front end of SERRATOME™

Figure 3B:
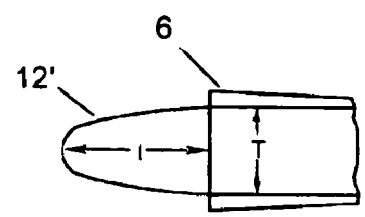
FIG. 3B is an orthogonal cross sectional view of a blunt front end that is parabolic in section.

FIG. 3B
6—serrations
12'—parabolic blunt front end of SERRATOME™

Figure 3C:
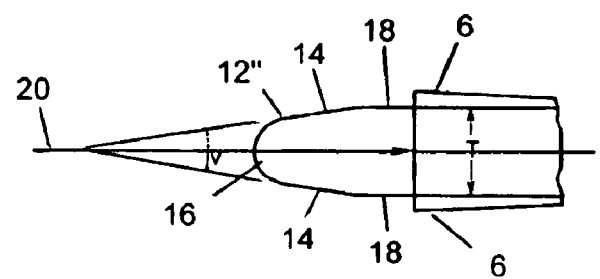
FIG. 3C is an orthogonal cross sectional view of a blunt front end that has a blunt nose and flat surfaces.
Figure 4:
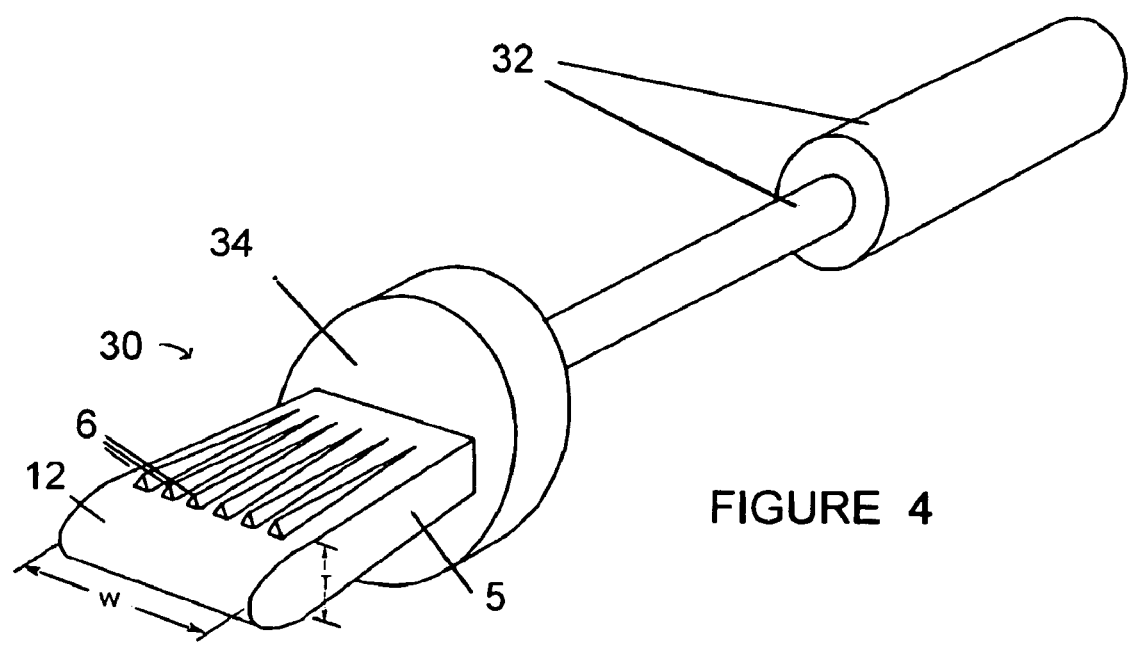
FIG. 4 is an oblique view of the present invention shown with a blunt front end and with a handle.

FIG. 3C
6—serrations
12"—facetted blunt front end of SERRATOME™
14—upper and lower flat inclined facets of blunt end
16—blunt front end of SERRATOME™
18—upper and lower parallel flat facets of blunt end
20—centerline FIG. 4
5—main body of SERRATOME™
6—serrations
12—blunt front end of SERRATOME™
30—SERRATOME™ with stop and handle
32—handle
34—stop

DESCRIPTION OF THE PREFERRED EMBODIMENTS

The present invention, which is called a SERRATOME™ is a bone-scraping or cutting device designed to be driven into an intervertebral space so as to remove, by cutting and/or abrading, a sufficient amount of end plate cortical bone of two adjacent vertebral bodies to allow blood to flow into the intervertebral space from the cancellous region of the respective vertebral bodies. Establishment of the flow of blood from within the adjacent vertebral bodies, and the initiation of the clotting of that blood, can be sufficient preparation of the intervertebral site for the installation of an allograft implant. That is, the flow of blood into the implant and the intervertebral space around it will initiate clotting in and around the implant, which clotting is believed to promote new bone growth.

The SERRATOME™ cutter invention is different from the dovetail cutter, or dovetome, of U.S. Pat. No. 6,096,080 in that the SERRATOME™ is not intended to provide for subsequent mechanical locking of the allograft implant to the adjacent vertebral bodies. In fact, part of the purpose of the present invention is to prepare the implant site in a way that does not destroy or remove a large amount of endplate cortical material, but rather scrapes away only an amount of the cortical material sufficient for blood from the cancellous regions to seep into the region where the allograft implant is to be installed. Once the flow of blood has been established, the region is prepared to receive an allograft implant.

Referring to FIG. 1, there is shown, in oblique view, the SERRATOME™ 2 according to the present invention. It comprises a hollow rectangular solid 4 having sharp serrations or teeth 6, shaped so as to present the maximum tooth surface along the side 7, and bottom side 9 of the sharpened front edge 8 of the SERRATOME™.

FIG. 2A shows in orthogonal view a front view of the SERRATOME™ 2, with the cutting edge 8, with serrated cutting teeth 6 being on the front side, that is, the portion of the SERRATOME™ that is driven first into the intervertebral space. The SERRATOME™ 2 has a width of W and a thickness of T. FIG. 2B is an orthogonal side view of the SERRATOME™ 2, showing the front cutting edge 8 with serrated teeth 6 on the top and bottom sides. It has a body length of L. FIG. 2C is an orthogonal top view of the SERRATOME™ invention 2 showing the conformation of the teeth 6 in relation to the top of the hollow rectangular body 4 of the invention. (The conformation of the teeth 6 on the bottom side, not shown, is the same as on the top side.) The areas of the top and bottom faces or surfaces (FIG. 2C) are larger than the other surfaces of the rectangular body of the SERRATOME™.

FIGS. 1, 2A, 2B and 2C show the basic SERRATOME™ invention in a simplified form, i.e., they show the basic invention with sufficient detail to convey implicitly to those skilled in the art the invention's operation. That is, the front edge 8 is inserted, from the anterior direction, or perhaps from a partially or fully lateral direction, into the space between two mutually adjacent vertebral bodies to be fused. The insertion process takes place after all or most of the tissues normally located between the adjacent vertebrae being fused has been removed, including the intervertebral disc or portions thereof. As the SERRATOME™ 2 is inserted into the intervertebral space, the upper and lower sets of serrations 6, impact against and remove by scraping portions of the cortical bone of the respective endplates of the vertebral bodies. Cortical bone chips that are removed by the serration are able to move into the hollow volume of the SERRATOME™, thereby allowing their easy removal when the SERRATOME™ is extracted from the intervertebral space after the termination of its cutting action.

The width W of the serrate is on the order of the width of the region into which the allograph implant is to be placed. The thickness T is approximately the intervertebral distance that separates the vertebral bodies when they are optimally distracted; that is, the thickness T depends upon the thickness of the intervertebral space in such a way that the surgeon can select, from a set of SERRATOMES™ of differing thicknesses, the serrate having the optimal thickness T for the intervertebral space being worked upon. For example, the spacing between vertebrae is greater in the lumbar region than in the thoracic region and, in the cervical region, the intervertebral spacing is small, as are the vertebrae of the cervical portion of the spine. The length L of the serrate is less than the distance between the anterior faces of the vertebral bodies and spinal cord.

FIG. 3A shows in oblique view another embodiment of a serrate 10 having serrations 6 on the top and bottom (the latter not visible in the oblique view). A blunted front region 12, located forward of the serrated teeth 6 projects out ahead of the main body 5 of the serrate 10. The purpose of the outward-projected blunt front region 12 is to provide guidance of the serrate into the intervertebral space while simultaneously distracting or separating the vertebral bodies between which the serrate is being inserted and guiding the serrated teeth 6 into position for an optimal abrading interaction with the cortical endplate surface material of the vertebral bodies.

As described above in relation to the basic serrate invention, the width W is on the order of the width of the region into which the allograph implant is to be placed. The thickness T of the serrate is approximately the distance that separates the vertebral bodies when they are maximally distracted; that is, the thickness T depends upon the thickness of the intervertebral space in such a way that the surgeon can select from a set of SERRATOMES™ of differing thicknesses the one having the optimal thickness T for the intervertebral space being prepared for allograph type implantation. And the length L' of the serrate and its projected bullet-shaped blunt front is less than the distance between the anterior faces of the vertebral bodies and spinal cord.

FIGS. 3B and 3C show cross-sectional shapes of the projected front of the serrate 10. The length L'' of the projected region is on the order of twice the thickness T of the serrate 10, i.e., adequately long to guide the serrate into position to perform its cutting operation upon the cortical endplates, but not long enough to interfere with the depth of cut of the teeth 6. In FIG. 3B, the shape of the projected front 12' is essentially that of a parabola. In FIG. 3C, the shape of the projected front 12'' is comprised of a blunt tip 16, circular, parabolic or ogive in shape, joining with flat inclined faces 14 which are arranged symmetrically with one another in relation to the centerline 20. The flat faces 14 have an angle v in relation to one another. The projected front 12'' further consists of parallel flat surfaces 18 separated by the width T such that the most separated portions of the angled flat surfaces 14 are displaced by a distance u from the frontmost portions of the serrating teeth 6. The parallel flat surfaces 18 are to provide alignment guidance of the serrate into the intervertebral space in a way that is optimal for the cortical endplate abrading or cutting operation.

FIG. 4 is a view of a serrate cutter 30 affixed to a handle 32. There is shown provided in the serrate cutter 30 a stop 34 that is either part of the handle 32 or an intervening element that is joined between the serrate 30 and the handle portion 32. The stop 34 prohibits the serrate from going too deep into the intervertebral space, so as to minimize the risk of damage to the spinal cord lying anterior to the main portions of the vertebral bodies. The handle 32 may have affixed to its end most distal from the serrate cutter an anvil suitable for use with a mallet driver, or it may have affixed to it a simple handle which the surgeon can grasp so as to push the serrate into the intervertebral space for a single manual cutting motion or additional cutting motions. Or, additionally, the handle might have affixed to its distal end a pneumatic or hydraulic or other vibrating driver device that can, in an easily controllable way, allow the surgeon to move the serrate in its intended linear motions in the most efficient, safe and controllable way.

The inventors envision further that the foregoing serrate invention is intended to be used independently, without guiding tools or alignment jigs, or to be used in conjunction with the vertebral distractors and dovetail cutting guide apparatus like those described in U.S. Pat. Nos. 6,096,080 and 6,241,769, incorporated herein by reference hereto.

It will now be apparent to those skilled in the art that other embodiments, details, improvements and uses can be made consistent with the letter and spirit of the foregoing disclosure and within the scope of this patent, which is limited only by the following claims.

We claim:

1. A spine surgery instrument for cutting and removing a controlled amount of cortical endplate bone from at least one vertebral body adjacent to an intervertebral space remaining after excision of all or part of an intervertebral disc, said instrument comprising
   a tome having a body with a parallelepiped shape and having a distal end and a proximal end, said parallelepiped having a top surface and a bottom surface when inserted into the intervertebral space, said distal end having a blunt front end region, said top surface and said bottom surface having set back from the blunt front end of the distal end a plurality of sharp edged serrations configured to cut or abrade the endplate of the at least one vertebral body.

2. The instrument of claim 1 in which the parallelepiped shape is a truncated four sided pyramid.

3. The instrument of claim 1 in which the parallelepiped shape is a rectangular parallelepiped.

4. The instrument of claim 1 in which the serrations comprise the end edges of protrusions in the top surface and the bottom surface.

5. The instrument of claim 1 in which the blunted front end region comprises a tip that is circular, parabolic, or ogive in shape, joined with flat inclined faces which are arranged symmetrically with one another, joined with parallel flat surfaces.

6. The instrument of claim 1 further comprising a shaft having a first end connected to the proximal end of the tome, and a second end having attached thereto an extension for engagement with mechanical energy transmission means.

7. The instrument of claim 6 further comprising a depth stop on the shaft between the body and the extension.

* * * * *